(12) United States Patent
Eaton et al.

(10) Patent No.: US 7,931,025 B2
(45) Date of Patent: *Apr. 26, 2011

(54) PATIENT INTERFACE AND HEADGEAR CONNECTOR

(75) Inventors: Jason P. Eaton, Hunker, PA (US); Peter Chi Fai Ho, Pittsburgh, PA (US); Elias G. Diacopoulos, Export, PA (US); Lance Busch, Trafford, PA (US)

(73) Assignee: RIC Investments, LLC, Wilmington, DE (US)

( * ) Notice: Subject to any disclaimer, the term of this patent is extended or adjusted under 35 U.S.C. 154(b) by 946 days.

This patent is subject to a terminal disclaimer.

(21) Appl. No.: 11/449,111

(22) Filed: Jun. 8, 2006

(65) Prior Publication Data
US 2006/0225740 A1  Oct. 12, 2006

Related U.S. Application Data

(63) Continuation-in-part of application No. 10/629,366, filed on Jul. 29, 2003, now Pat. No. 7,066,179.

(60) Provisional application No. 60/402,335, filed on Aug. 9, 2002.

(51) Int. Cl.
| | |
|---|---|
| *A62B 9/04* | (2006.01) |
| *A62B 18/08* | (2006.01) |
| *A61M 16/00* | (2006.01) |
| *A44B 11/00* | (2006.01) |
| *A44B 1/04* | (2006.01) |
| *A44B 1/18* | (2006.01) |
| *A47C 5/06* | (2006.01) |
| *A41F 1/04* | (2006.01) |
| *A41F 1/00* | (2006.01) |

(52) U.S. Cl. ......... 128/206.24; 128/202.27; 128/207.17; 128/207.11; 128/206.27; 24/265 R; 24/265 BC; 24/630; 24/662; 24/686

(58) Field of Classification Search ............. 128/202.27, 128/207.17, 207.11, 206.27; 24/265 AC, 24/265 R, 662, 630, 686, 265 BC
See application file for complete search history.

(56) References Cited

U.S. PATENT DOCUMENTS

| | | | |
|---|---|---|---|
| 1,310,119 A | | 7/1919 | Harper |
| 2,097,676 A | | 11/1937 | Shindel et al. |
| 2,375,147 A | | 5/1945 | Teague |
| 3,433,222 A | | 3/1969 | Pinto |
| 3,441,020 A | | 4/1969 | Aasen et al. |
| 3,550,588 A | | 12/1970 | Stahl |
| 4,304,403 A | * | 12/1981 | Wilson .......................... 473/502 |
| 4,414,973 A | | 11/1983 | Matheson et al. |
| 4,437,462 A | | 3/1984 | Piljay et al. |
| 4,960,121 A | * | 10/1990 | Nelson et al. ............ 128/206.24 |
| 5,069,205 A | | 12/1991 | Urso |
| 5,086,768 A | | 2/1992 | Niemeyer |
| 5,502,878 A | | 4/1996 | Anscher |

(Continued)

FOREIGN PATENT DOCUMENTS

EP  0958841  11/1999

(Continued)

*Primary Examiner* — Patricia M Bianco
*Assistant Examiner* — Nihir Patel
(74) *Attorney, Agent, or Firm* — Michael W. Haas

(57) ABSTRACT

The present invention provides a connection device for connecting a headgear having straps, a mask and a system for supplying a flow of gas to a patient. The connection device incorporates a locking member or locking portion which is configured to lock the straps in a particular location.

21 Claims, 17 Drawing Sheets

U.S. PATENT DOCUMENTS

| | | |
|---|---|---|
| 5,517,986 A | 5/1996 | Starr et al. |
| 5,555,569 A | 9/1996 | Lane |
| 5,662,101 A | 9/1997 | Ogden et al. |
| 5,771,886 A | 6/1998 | Maire et al. |
| 5,924,420 A * | 7/1999 | Reischel et al. ......... 128/206.21 |
| 6,192,886 B1 | 2/2001 | Rudolph |
| 6,374,826 B1 | 4/2002 | Gunaratnam et al. |
| 6,578,572 B2 | 6/2003 | Tischer et al. |
| 6,691,314 B1 | 2/2004 | Grilliot et al. |
| 7,066,179 B2 * | 6/2006 | Eaton et al. .............. 128/206.27 |
| 2003/0196662 A1 | 10/2003 | Ging et al. |

FOREIGN PATENT DOCUMENTS

WO      WO 00/78383      12/2000

* cited by examiner

PATIENT INTERFACE AND HEADGEAR CONNECTOR

CROSS-REFERENCE TO RELATED APPLICATIONS

This application is a continuation-in-part of U.S. patent application No. 10/629,366 filed Jul. 29, 2003, now U.S. Pat. No. 7,066,179, which claims priority under 35 U.S.C. § 119(e) from provisional U.S. patent application No. 60/402,335, filed Aug. 9, 2002, the contents of which are incorporated herein by reference.

BACKGROUND OF THE INVENTION

1. Field of the Invention

The present invention generally relates to a device used in a patient interface assembly to connect a headgear and a patient interface device, such as a mask, and to a system for supplying a flow of gas to a patient.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle or the patient's condition, to treat a medical disorder, such as sleep apnea syndrome, in particular, obstructive sleep apnea (OSA), cheynes-stokes respiration, or congestive heart failure.

Non-invasive ventilation and pressure support therapies involve the placement of a patient interface device, which is typically a nasal or nasal/oral mask, on the face of a patient to interface the ventilator or pressure support device with the airway of the patient so that a flow of breathing gas can be delivered from the pressure/flow generating device to the airway of the patient. It is known to maintain such masks on the face of a patient by means of a headgear worn on the patient's head. A typical headgear assembly includes upper and lower straps, each having opposite ends that thread through connecting elements provided on the opposite sides of the mask. Because such masks are typically worn for an extended period of time, it is important the headgear maintain the mask in a tight enough seal against a patient's face without discomfort.

One such headgear is disclosed in U.S. Pat. No. 5,517,986. The headgear includes a cap-like headpiece adapted to fit the crown and back of a patient's head. Lower straps provide a two-point connection with a gas delivery mask. Additionally, a pair of upper straps can be used to provide a four-point connection with the gas delivery mask if needed. In order to secure the mask in place on a patient's head, each strap passes through an elongated opening on the mask and then bends back on itself to hold in place with hook and loop material. The patient adjusts the length of material that passes through the opening to secure a good fit of the mask. However, if the mask is removed, the adjustment process must be repeated.

Another known mask and headgear connector arrangement is disclosed in International Publication No. WO 00/78383 A1 ("the '383 application"). In this arrangement, a respiratory mask has a rigid frame having first and second female connectors integrally molded thereto. The female connectors receive male connectors connected to the headgear straps. The female connectors are locked into a single discrete location when engaged. Because the connectors do not swivel independently, the user must take care to ensure that each strap is not twisted when the connectors are engaged. If a strap does become twisted, the user must disconnect the male connectors, straighten the strap and reconnect the male connectors, otherwise the twist of the strap may dislodge the mask from the user.

Published European patent application publication no. EP 0958841 A2 (application no. 99108650.5) discloses a mask and headgear connection assembly that is similar in function to that disclosed in the '383 application. In the European application, loops are provided at the end of the headgear straps and corresponding hooks are provided on the mask shell. This configuration allows the user the easily detach the headgear straps from the mask by removing the loops from the hooks. However, this hook and loop configuration suffers from the same disadvantage as that of the '383 application. Namely, it does not allow the connectors to swivel independently so that twisting of the headgear straps can deteriorate the usefulness of the mask.

SUMMARY OF THE INVENTION

Accordingly, it is an object of the present invention to provide a connection assembly for coupling a patient interface device and a headgear that overcomes the shortcomings of conventional mask/headgear connectors.

An exemplary embodiment of the present patient interface device includes a shell and a first connector associated with the shell. The interface also includes a second connector which in configured to connect the shell with a headgear assembly. The second connector has a locking portion which securely holds at least one strap of the headgear assembly and a bulbous portion which engages the first connector.

Another exemplary embodiment of the present patient interface device includes a shell and a forehead support extending from the shell. The interface also includes a forehead member attached to the forehead support. In this embodiment of the invention, the forehead member includes a locking member which is configured to secure a headgear assembly to the interface.

An exemplary embodiment of the present patient interface device includes a shell and a first connector associated with the shell. The interface also includes a second connector which in configured to connect the shell with a headgear assembly. The second connector has a locking portion which securely holds at least one strap of the headgear assembly and a bulbous portion which engages the first connector. The interface also includes a forehead member attached to the forehead support. In this embodiment of the invention, the forehead member includes a locking member which is configured to secure a headgear assembly to the interface.

Another exemplary embodiment of the patient interface assembly includes a shell and a headgear assembly having at least one strap. In this embodiment the assembly further includes a strap connector connected to the headgear having a locking portion to secure the strap in place.

Another exemplary embodiment of the patient interface assembly includes a shell and a first connector associated with the shell. The assembly further includes a second connector adapted to be connected to a headgear assembly having at least one strap for securing the mask on a user. In this embodiment, the second connector includes a bulbous portion having a socket. The socket is configured to receive a bulbous portion on the mask.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 18B is a cross-sectional view of the third alternative strap connector of FIG. 18a;

DETAILED DESCRIPTION OF THE PRESENTLY PREFERRED EMBODIMENTS OF THE INVENTION

FIGS. 1-4 illustrate an exemplary embodiment of a patient interface assembly 8 including a gas delivery mask 10 and a headgear assembly 12 according to the principles to the present invention. More specifically, these figures illustrate a gas delivery mask 10, which functions as a patient interface device to communicate a flow of breathing gas between a patient's airway and a pressure generating device 14. Examples of pressure generating devices include a ventilator, CPAP device, or variable pressure device, e.g. an auto-tritrating CPAP device or a BiPAP® device manufactured and distributed by Respironics, Inc. of Pittsburgh, Pa., in which the pressure provided to the patient varies with the patient's respiratory cycle so that a higher pressure is delivered during inspiration than during expiration.

Figure 1:
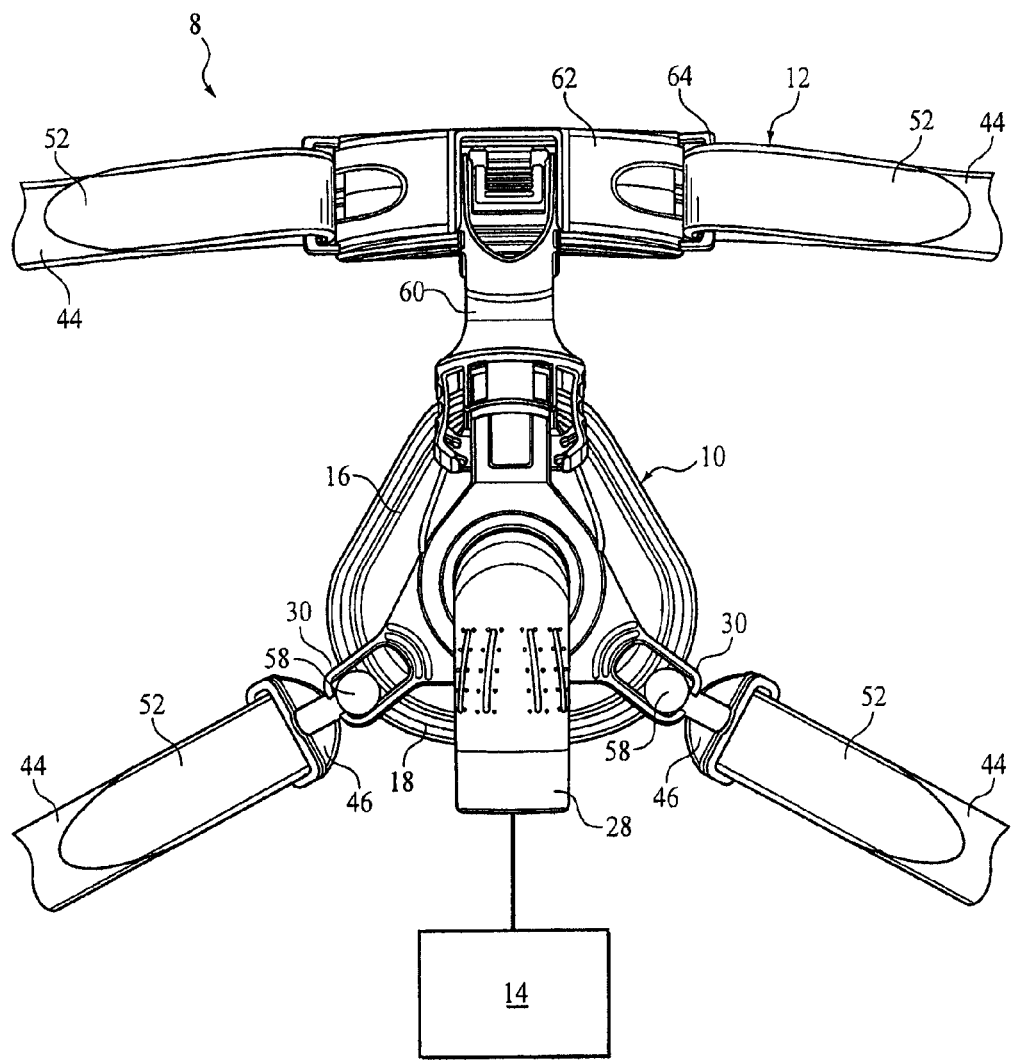
FIG. 1 is a front view of the patient interface assembly according to the principles of an exemplary embodiment of the present invention shown (schematically) connected to a gas flow generating device.
Figure 2:
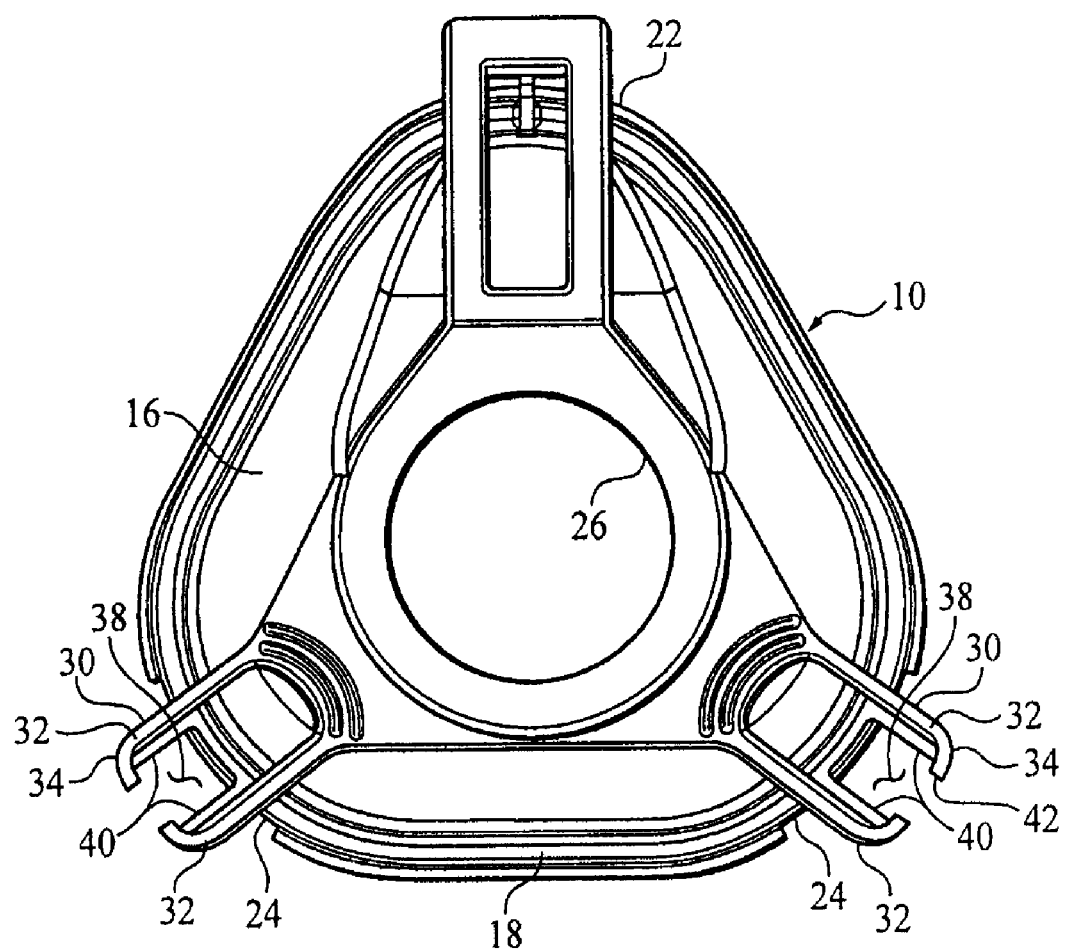
FIG. 2 is a front view of the mask shell in the patient interface assembly of FIG. 1.
Figure 3:
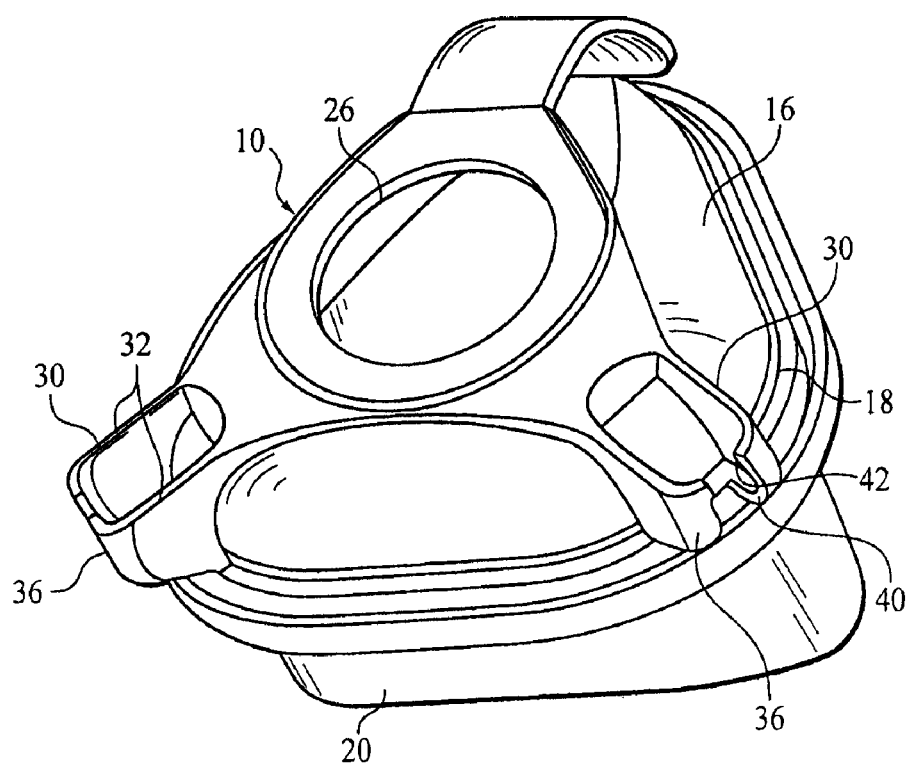
FIG. 3 is a perspective view of the mask shell in the patient interface assembly of FIG. 1.

Referring to FIGS. 1-3, there is illustrated a gas delivery mask 10 including a mask shell 16 or body portion that is preferably, but not necessarily, a generally rigid structural shell having an open side that defines an annular portion 18 to which a resilient, relatively soft seal member 20 or cushion is attached. In the illustrated exemplary embodiment, mask shell 16 is substantially triangular in shape, having an upper apex angle 22 and two lower angles 24. Mask shell 16 includes an inlet opening 26 adapted to receive a gas supply conduit 28. Seal member 20 is configured to receive a portion of the patient, such as the nose. Alternatively, mask 10 may, instead, comprise a nasal/oral mask configured to enclose the nose and mouth of a patient, or an oral mask configured to enclose only the mouth of a patient. Seal 20 defines the portion of the mask that contacts the user.

In the illustrated exemplary embodiment, a pair of first connectors 30 are rigidly attached to lower angles 24 of mask shell 16. Each first connector 30 includes relatively thin parallel walls 32, as perhaps best shown in FIG. 2, that project from lower angles 24 of the shell past annular portion 18. At distal ends 34 of the parallel walls, a notched wall 36 abuts the parallel walls and curves downward toward the annular portion 18 at lower angle 24 of mask shell 16. This is best shown in FIG. 3. Notched wall 36 includes a notch 38 or slot, extending throughout the length of the notched wall, having substantially parallel walls 40 and a small area 42 of reduced width near an upper edge of parallel walls 40.

Headgear straps 44 in headgear assembly 12 are selectively connected to mask 10 by means of a second connector 46. In the illustrated embodiment, a pair of second connectors 46, which are also referred to as strap connectors, are removeably connectable to end portions of headgear straps 44 and are also removeably connectable to first connectors 30 on each side of shell 16. The present invention contemplates that headgear assembly 12 can be any suitable headgear, i.e., and conventional headgear used in the patient interface field. For example, a typical headgear assembly comprises a headpiece (not shown) that overlies a portion of the patient's crania and headgear straps 44 extending therefrom to adjustably connect the headgear to the mask.

Figure 4:
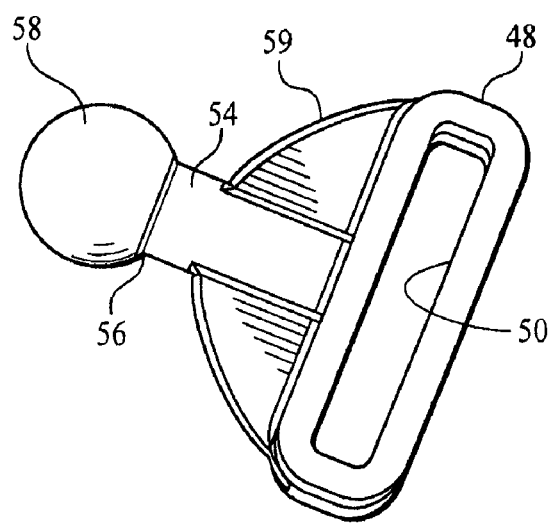
FIG. 4 is a perspective view of a strap connector in the patient interface assembly of FIG. 1 according to the principles of an exemplary embodiment of the present invention.

Each strap connector 46, as best seen in FIG. 4, includes an elongated portion 48 having an elongated opening 50. In a preferred embodiment, elongated portion 48 is rigid. However, the present invention also contemplates that portion 48 can be formed from a pliable or flexible material. In the illustrated embodiment, an end potion 52 of headgear strap 44 is threaded through elongated opening 50 and then bent back on itself to adhere hook and loop elements on the headgear strap connector 46. It is to be understood however, that any conventional technique for securing the end portion of the headgear strap to itself, such as a snap, buckle, or locking clamp, is contemplated by the present invention. In addition, the present invention contemplates a more permanent attachment of the end portion of the headgear strap to strap connector 46. For example, once the patient/user has set the headgear strap to the desired length and threaded in through opening 50, the free end of the strap can be permanently fixed back onto the strap, such as by gluing, sewing, or riveting the overlapping straps together.

Figure 5:
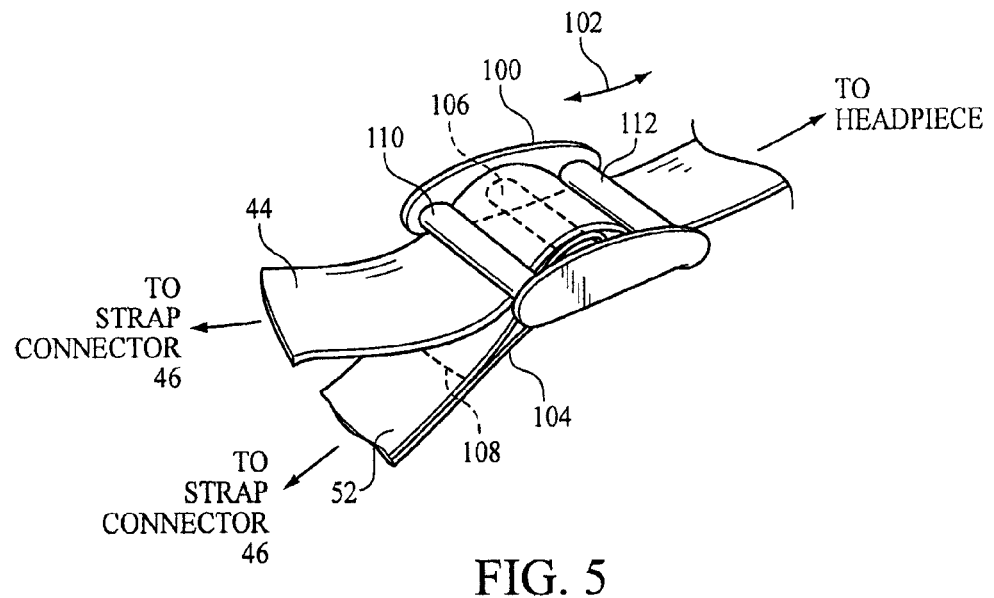
FIGS. 5 and 6 are perspective views of alternative designs for a headgear strap fastener clamp suitable for use with the headgear assembly of the present invention.
Figure 6:
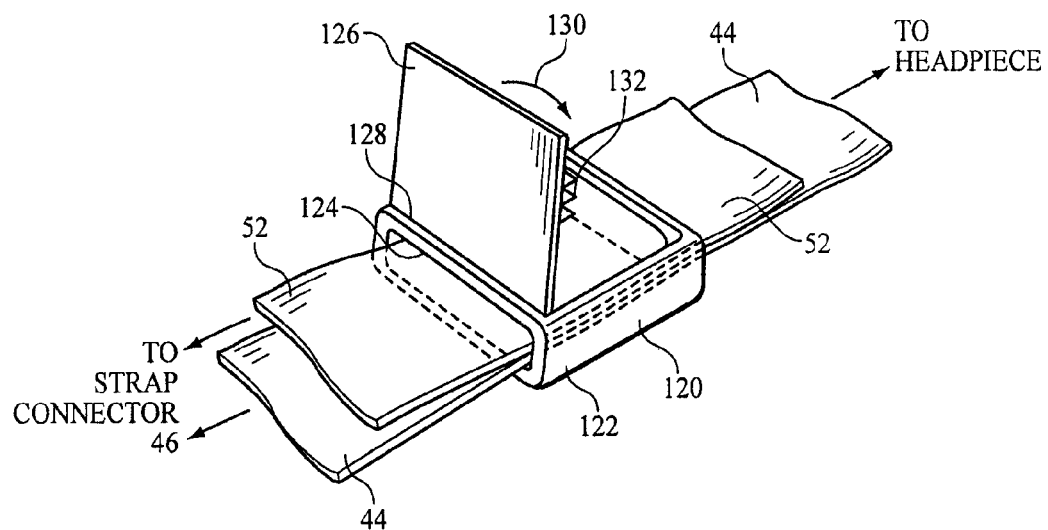

Two examples of locking clamps 100 and 120 that attach the end portion of the headgear strap to the rest of the strap are shown in FIGS. 5 and 6. Locking clamp 100 in FIG. 5 corresponds to a well known mechanism for attaching a free end of a strap to the remaining portions of the strap while allowing the position of the clamp relative to strap 44 to be moveable, as indicated by arrow 102. More specifically, a free end 104 of strap end portion 52 is secured to a center post 106 of clamp 100. For example, it is well know to stitch free end 104 to strap end portion 52, as indicated by dashed stitch line 108. Strap end portion 52 is threaded through strap connector 46 and then through posts 110 and 112 on clamp 100. In this manner, the length of the headgear strap from the headpiece to the strap connector can be adjusted and then maintained at the desired setting due to the binding effect of posts 108, 110 and 112 on the headgear strap.

Locking clamp 120 in FIG. 6 includes a body member 122 having a channel 124 defined therethrough so that the headgear straps 44 can pass through the body member. A clamping member 126 is attached to body member 122 via a hinge 128, such as a living hinge, so that the clamping member can close into an engaged relation with body member 122, as indicated by arrow 130. In the closed position (not shown), clamping member 126 pinches end portion 52 to a remaining portion of strap 44, thereby locking the strap in place. End portion 52 of strap 44 can be trimmed to remove excess length. Also, locking teeth 132 can be provided on clamp member 126. Although not illustrated, the present invention contemplates any conventional technique for securing clamp member 126 in the closed position, i.e., in an engaged relation with body member 122.

Referring again to FIGS. 1-4, strap connector 46 further includes a post portion 54 extending from the midpoint of the elongate portion. In a preferred embodiment, post portion 54 is rigid. However, the present invention also contemplates that post portion 54 can be formed from a pliable or flexible material. At a distal end 56 of post portion 54, opposite elongated portion 48, is a bulbous portion 58 of a diameter that is larger, e.g., twice the diameter, of post portion 54. Post portion 54 may also include web members 59 to support the post portion. It can be appreciated that shapes other than the sphere shown in the figures are contemplated for bulbous portion 58.

To connect headgear straps 44 to mask 10, each post portion 54 is placed in a respective notch 38 on first connector 30. Small area 42 of reduced width provides a zone of interference between notch 38 and post portion 54, such that post portion 54 snaps in place in the notch. Bulbous portion 58 has a diameter larger than the notch width and maintains strap connector 46 within first connector 30. When strap connector 46 is placed in first connector 30, it is free to swivel a full 360 degrees about its axis, as well as rotate angularly through substantially 90 degrees of angular rotation about each of its other two axes. Once strap connector 46 and first connector 30 are engaged, the user is free to adjust and straighten the headgear straps 44, and lock the length of the strap at the desired setting as discussed above. Thereafter, the headgear can be easily disconnected from the mask by disengaging bulbous portion 58 from first connector 30.

In the illustrated exemplary embodiment of patient interface assembly 8, mask 10 includes a forehead support arm 60 to which is attached a forehead member 62. Forehead member 62 functions in the same manner as conventional forehead assemblies. Namely, it provides additional connections to which headgear straps 44 in headgear assembly 10 can be coupled to the forehead member. For example, in the embodiment illustrated in FIG. 1, headgear straps 44 are coupled to a snap element 64 that selectively engages forehead member 62 in any conventional manner. It can be appreciated, however, that the ball-and-socket configuration for first connector 30 and strap connector 46 can also be used in conjunction with forehead member 62 for selectively and rotatably attaching the headgear straps to the forehead member. Of course, snap element 64 can also be eliminated in favor of a more permanent attachment of the headgear strap to forehead member 62.

Alternative exemplary embodiments of the patient interface assembly of the present invention are illustrated in FIGS. 7-26. In these embodiments, many features are similar to those illustrated in FIGS. 1-4. It should be noted that the forehead assembly is not shown in FIGS. 7-14, because the relevant features and alternative configurations of the mask and headgear connector of the present invention can be garnered from the connection shown on the mask shell. However, the configurations for coupling the headgear to the mask shell shown in FIGS. 7-14 and described below are equally applicable to attaching the headgear to the forehead member or other similar forehead assembly.

Figure 7:
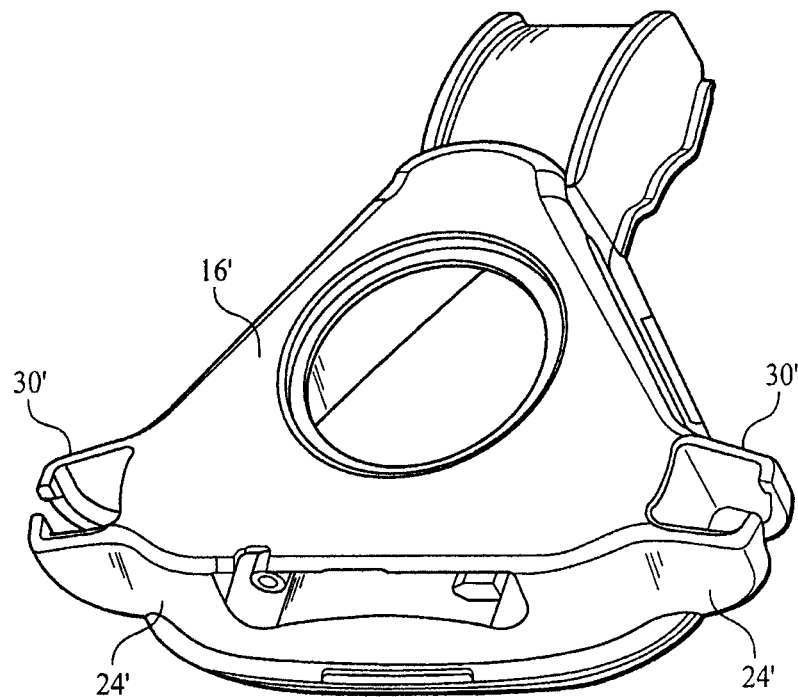
FIG. 7 is a perspective view of a second embodiment of a mask shell according to the principles of the present invention.
Figure 8:
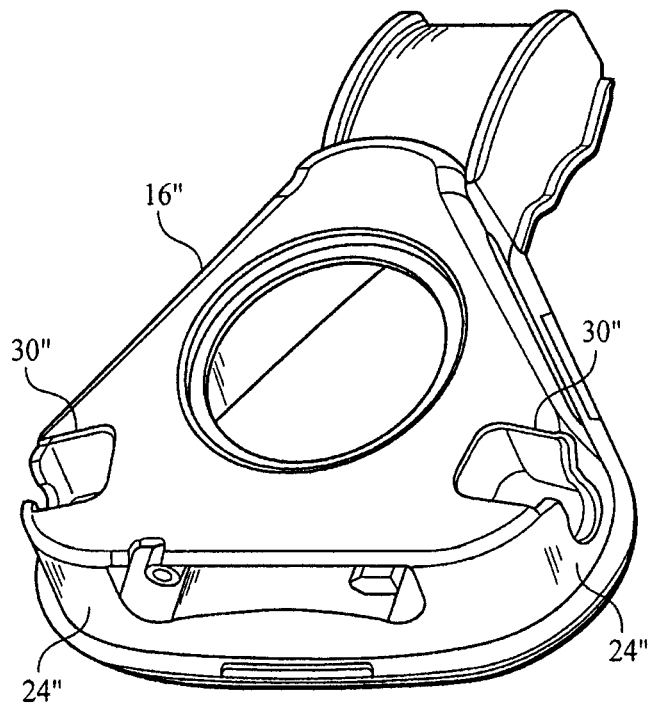
FIG. 8 is a perspective view of a third embodiment of a mask shell according to the principles of the present invention.
Figure 9:
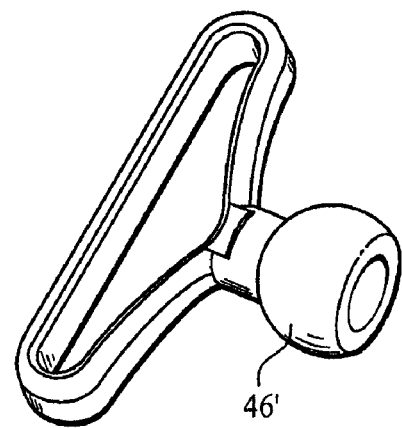
FIG. 9 is a perspective view of a second embodiment of a strap connector according to the principles of the present invention.
Figure 10:
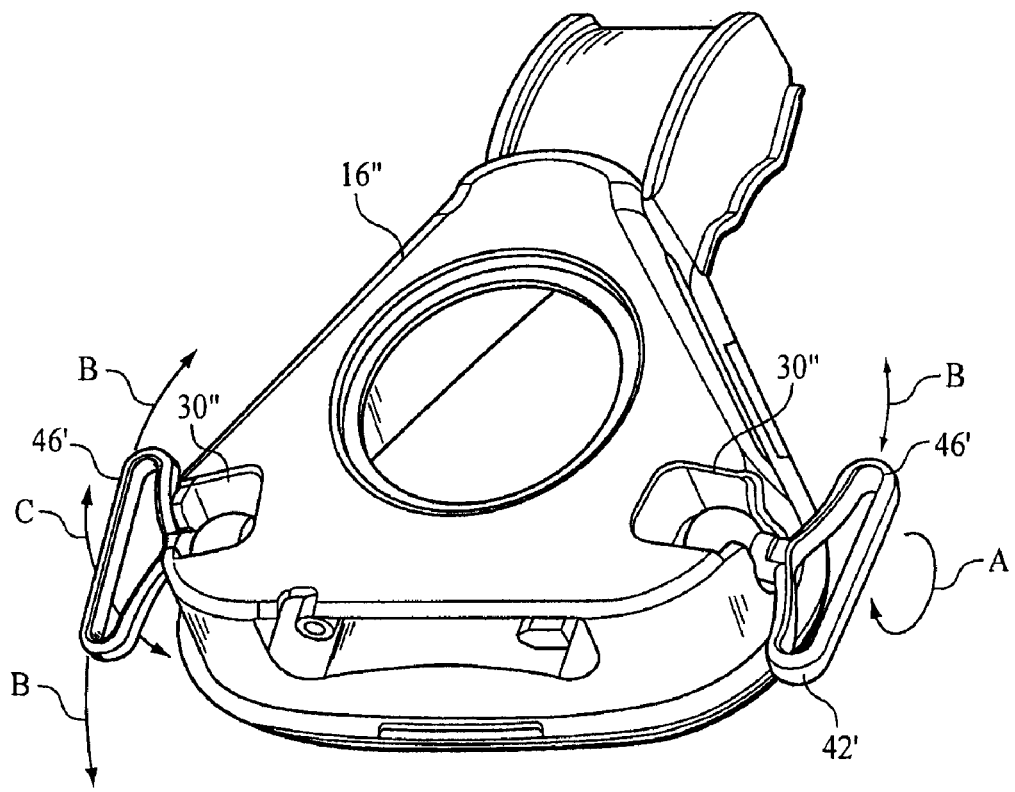
FIG. 10 is a perspective view of the mask shell shown in FIG. 9 and the strap connector shown in FIG. 8 illustrated in an engaged relation.
Figure 11:
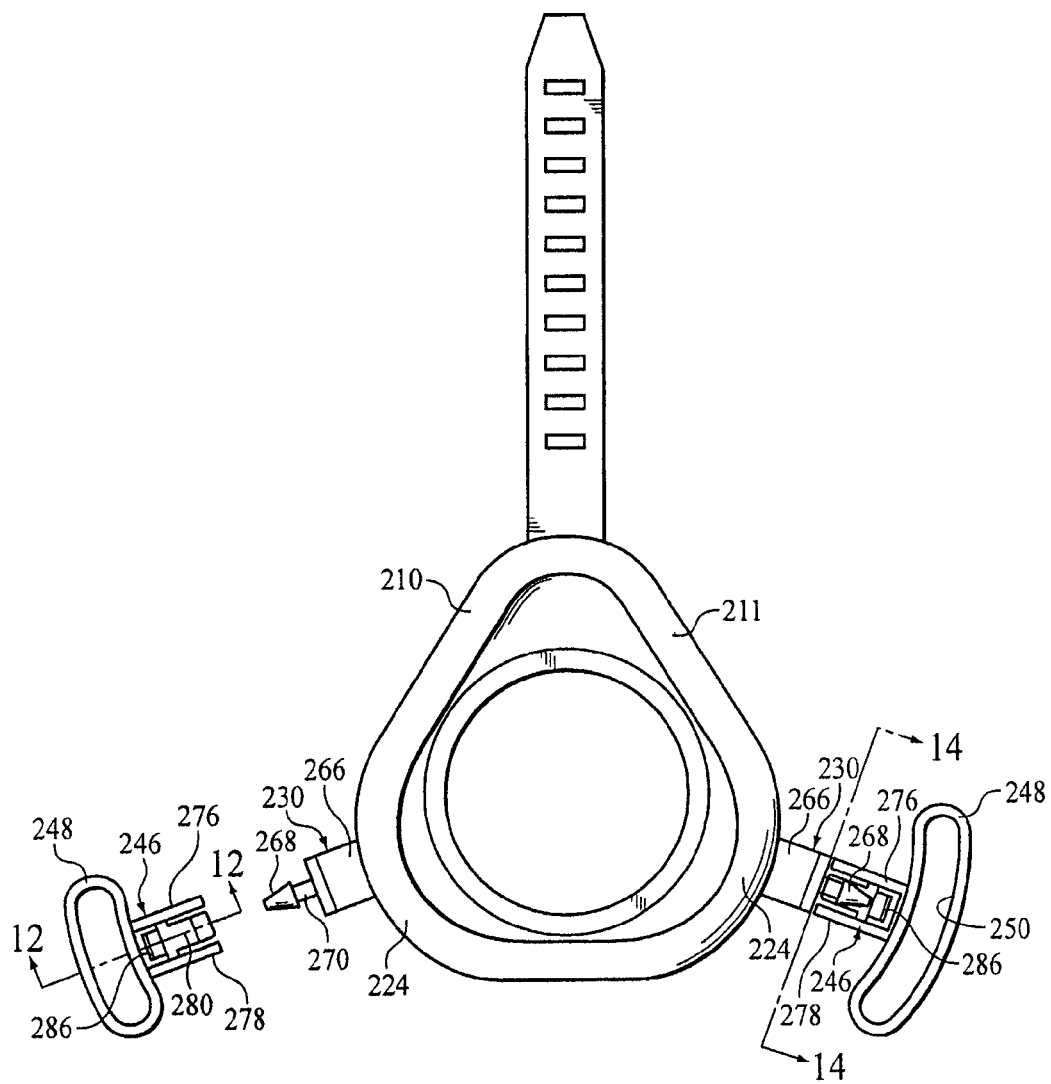
FIG. 11 is a partially exploded front view of a further embodiment of a patient interface assembly according to fourth embodiment of the present.
Figure 12:
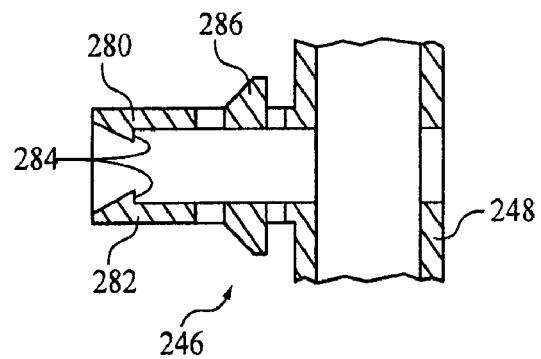
FIG. 12 is a cross-sectional view of the strap connector taken along line 12-12 in FIG. 11.
Figure 13:
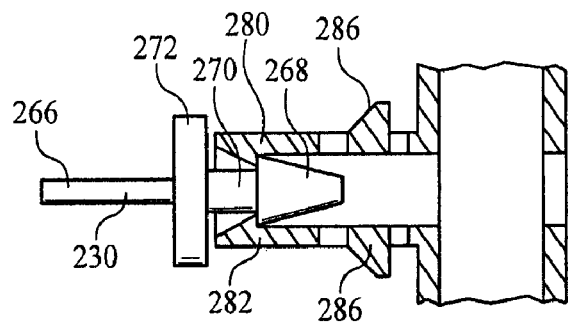
FIG. 13 is a partial cross-sectional view of a first connector connected to the strap connector in the mask assembly of FIG. 11.
Figure 14:
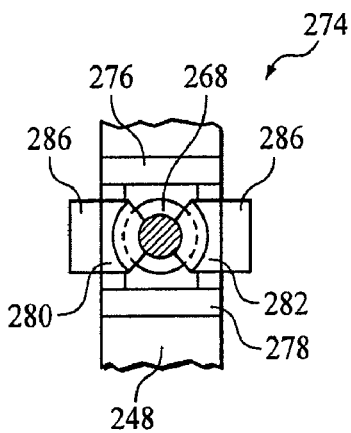
FIG. 14 is a cross-sectional view of the strap connector and first connector taken along line 14-14 of FIG. 11.

FIGS. 7 and 8 illustrate alternative embodiments for the mask shell, which are generally similar to mask shell 16 in FIGS. 1-3. However, mask shell 16' in FIG. 7 includes first connectors 30' that extend substantially perpendicularly from the lower angles 24' of the shell 16'. In the embodiment shown in FIG. 8, first connectors 30" are molded into mask shell 16", rather than protruding therefrom as in the previous embodiments. FIG. 9 illustrates an alternative embodiment for strap connector 46', and FIG. 10 shows how strap connectors 46" of FIG. 9 attach to mask shell 16" of FIG. 8 via first connectors 30". These alternative embodiments are provided to allow those skilled in the art to appreciate the variety of different configurations that are possible for first connectors 30, 30', 30" and strap connectors 46, 46' while still adhering to the basic principles of the present invention. These basic principles being to allow the strap connectors to 1) selectively attach to the mask shell, 2) rotate over a 360 degree angle, as illustrated by arrow A in FIG. 10, 3) move over a range of angles in a first plane that is generally parallel to that of mask shell 16, as indicated by arrow B, and 4) move over a range of angles in a second plane that is generally perpendicular to the plane of mask shell 16, as indicated by arrow C in FIG. 10.

A further alternative exemplary embodiment of the connection between a mask 210 and the headgear according to the principles of the present invention is illustrated in FIGS. 11-14. In this embodiment, each first connector 230 associated with mask shell 216 includes a first post portion 266 extending from each lower angle 224 of mask shell 216. At the distal end of first post portion 266, a cone-shaped member 268 extends from a second post portion 270. A retaining portion 272, having a diameter that is orientated generally perpendicular to first and second post portions 266 and 270, separates the first and second post portions. Retaining portion 272 forms a groove-like channel between the base of cone-shaped shaped member 268 and retaining portion 272.

In an exemplary embodiment of the present invention, first post portion 266 is a substantially planar portion so that it flexes in a direction perpendicular to the plane in which the mask shell is oriented and does not flex in a direction parallel to the plane in which the mask shell is oriented. It can be appreciated, however, that first post portion 266 can have any one of a variety of configurations, including being rigid and immovable. In addition, the present invention contemplates eliminating first post portion 266 entirely.

Each strap connector 246 includes a rigid elongated portion 248 having an elongated opening 250. The strap connector 246 further includes a third post portion 274 extending from the mid-point of elongated portion 248. Third post portion 274 includes two opposed rigid walls 276, 278 and two opposed flexing walls 280, 282 having internal semi-circular latching teeth 284 for engaging the groove formed at the base of cone-shaped member 268 of first connectors 230. The latching teeth 284 are releasable by pressing protrusions 286 on the outside of flexing walls 280 and 282.

Once latching teeth 284 engage with the groove on the first connector, it provides a secure connection that allows for a 360° rotation of the strap connector relative to the first connector. Additionally, the flexibility of the relatively thin post portion 270 allows for movement of the strap connector along two axes so that the strap connectors can provide a connection with the headgear straps that enable the straps to more closely conform to the facial contour of the user, i.e., do not protrude irregularly from the face of the user. It should be noted that the present invention contemplates that second post portion 270 can have any one of a variety of shapes and sizes to provide any desired range of flexing in any desired direction or directions.

Figure 15:
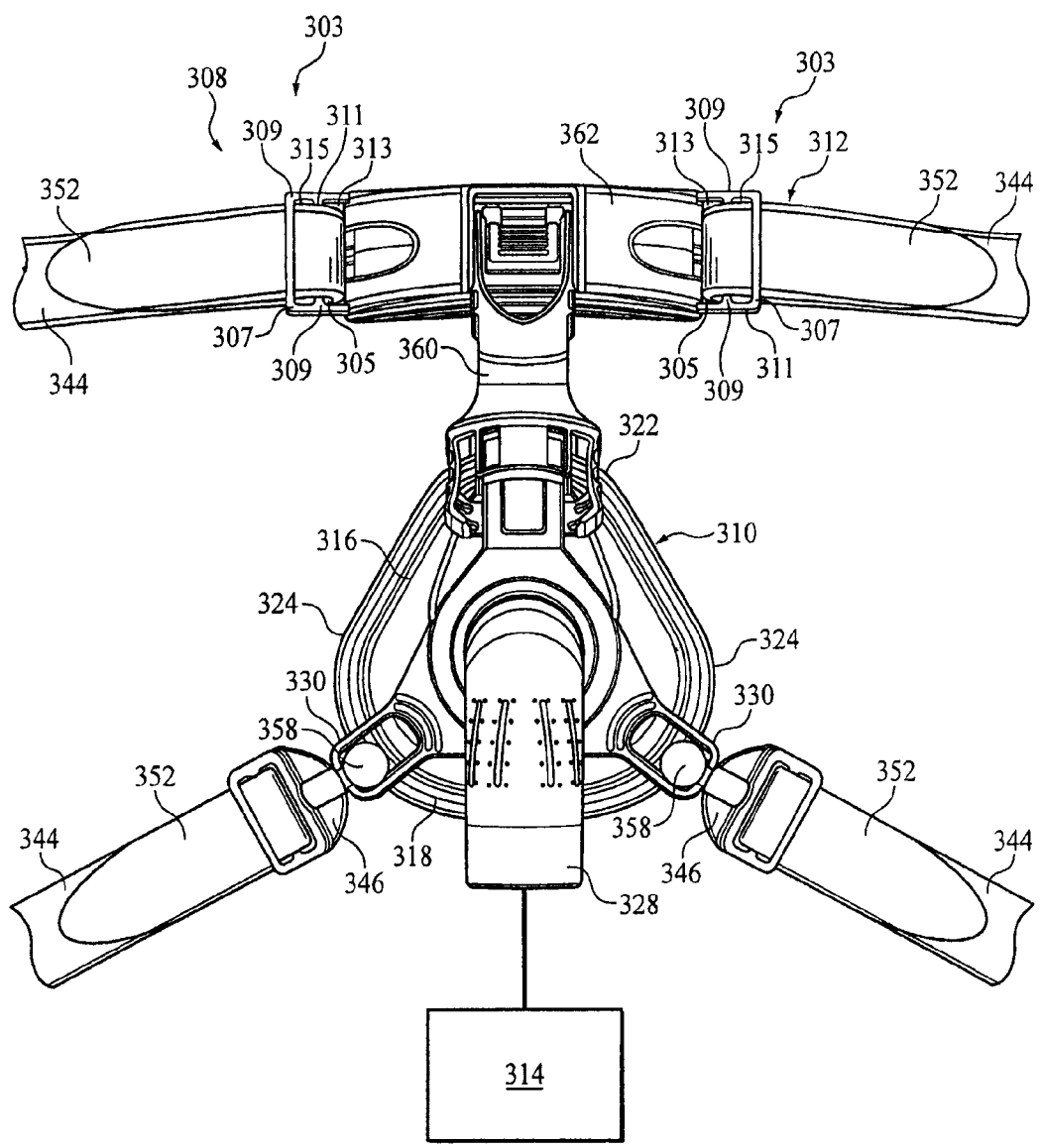
FIG. 15 is a front view of an alternative embodiment of the patient interface assembly according to the principles of an exemplary embodiment of the present invention shown (schematically) connected to a gas flow generating device.
Figure 16:
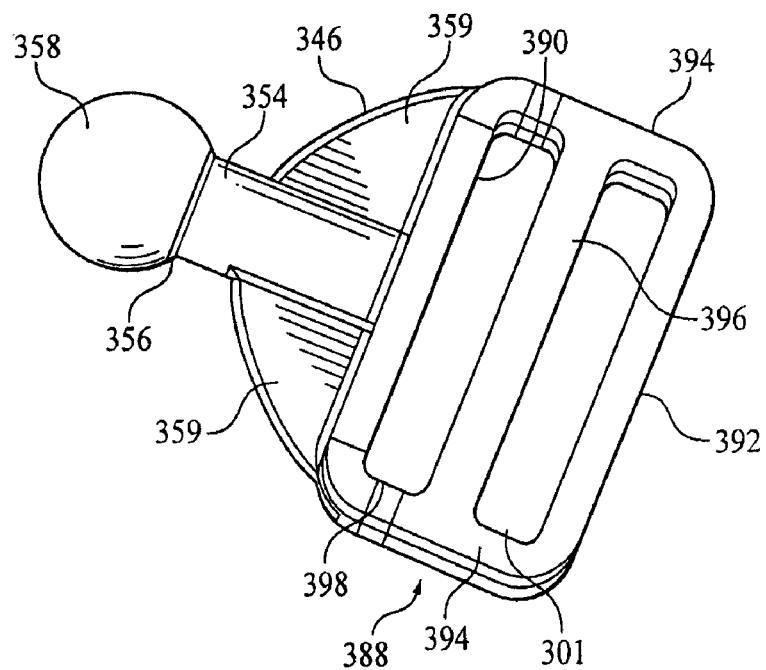
FIG. 16 is a perspective view of the first alternative strap connector of FIG. 15.

In another alternative embodiment, a patient interface 308, as shown in FIGS. 15 and 16, includes a gas delivery mask 310 and a headgear assembly 312. More specifically, these figures illustrate a gas delivery mask 310, which functions as a patient interface device to communicate a flow of breathing gas between a patient's airway and a pressure generating device 314.

The gas delivery mask 310 includes a mask shell 316 or a body portion that is preferably, but not necessarily, a generally rigid structural shell having an open side that defines an annular portion 318 to which a resilient, relatively soft seal member or a cushion is attached. In the illustrated exemplary embodiment, mask shell 316 is substantially triangular in shape, having an upper apex angle 322 and two lower angles 324. Mask shell 316 includes an inlet opening adapted to receive a gas supply conduit 328. Attached to the mask shell is a seal member 320 which is configured to receive a portion of the patient, such as the nose. Alternatively, mask 310 may, instead, comprise a nasal/oral mask configured to enclose the nose and mouth of a patient, or an oral mask configured to enclose only the mouth of a patient. The seal defines the portion of the mask that contacts the user. The seal and inlet opening are substantially the same as seal 20 and air inlet 26 as shown in FIG. 3.

In the illustrated exemplary embodiment, a pair of first connectors 330 are rigidly attached to lower angles 324 of mask shell 316. Headgear straps 344 in headgear assembly 312 are selectively connected to mask 310 by a second connector 346. In the illustrated embodiment, a pair of second connectors 346, which are also referred to as strap connectors, are removably connectable to end portions of headgear straps 344 and are also removably connectable to first connectors 330 on each side of shell 316. The present invention contemplates that headgear assembly 312 can be any suitable headgear, i.e., and conventional headgear used in the patient interface field. For example, a typical headgear assembly comprises a headpiece (not shown) that overlies a portion of the patient's crania and headgear straps 344 extending therefrom to adjustably connect the headgear to the mask.

Strap connector 346 includes a locking portion 388 having a first elongate member 390 and a second elongate member 392. The elongate members terminate at a pair of side members 394. The locking portion 388 also includes a divider 396 defining a first opening 398 and a second opening 301. The strap connector 346 further includes a post portion 354 extending from the midpoint of the locking portion 388. The strap connector 346 includes web portions 359 to support post portion 354. At a distal end 356 of post portion 354 is a bulbous portion 358 of a diameter that is larger, e.g., twice the diameter, of post portion 354. It can be appreciated that shapes other than the sphere shown in the figures are contemplated for bulbous portion 358. The headgear straps 344 are connected to the mask via locking portions 388. Locking portions include elongate members 390, 392 between a pair of side members 394. A divider 396 is located between the elongate members 390, 392 to define a pair of openings 398, 301.

It can be appreciated that shapes other than the sphere shown in the figures can be used for bulbous portion 358. As such, locking portion 388 thus forms a buckle-like structure to secure the end portion of the headgear strap. This feature may be used alone to secure the strap at a given length or it may be used in combination with other fasteners. For instance, the headgear strap 344 may include hook and loop elements such that the end portion of the strap may be bent back upon itself and adhered in place. It is understood however, that any convention technique for securing the end portion of the headgear strap to itself, such as a snap, buckle, or locking clamp, is contemplated by the present invention.

When strap connector 346 is placed in first connector 330, it is free to swivel a full 360 degrees about its axis, as well as rotate angularly through substantially 90 degrees if angular rotation about each of its other two axes. Once strap connector 346 and first connector 330 are engaged, the user is free to adjust and straighten the headgear straps 344, and lock the length of the strap. Alternatively, strap connector 346 may be integrally formed with, or fixedly connected to, the mask 310 to further minimize the number of parts utilized and the potential loss of connector 346.

In the illustrated exemplary embodiment of patient interface assembly 308, mask 310 also includes a forehead support 360 to which is attached a forehead member 362. Forehead member 362 functions in the same manner as conventional forehead assemblies. Namely, it provides additional connections to which headgear straps 344 in headgear assembly 312 can be coupled to the forehead member. For example, in the embodiment illustrated in FIG. 15, headgear straps 344 are coupled to locking element 303 having elongate members 305, 307 between side members 309. A divider 311 defines a pair of openings 313, 315. Headgear strap end portion 352 is threaded into opening 313, over divider 311, and down through opening 315.

Locking portion 388 and locking element 303 both incorporate a buckle-like structure such that strap 344 may be held in place. One unique aspect of this embodiment is that this buckle-like structure is integrated into locking portion 388 and locking element 394 rather than using a separate part which could be misplaced. As an alternative to the structure depicted in FIGS. 15 and 16, this structure could take on a variety of other constructions. For instance, locking clamps 100 and 120, as described above, could be integrated into locking portion 388 and locking element 303.

Figure 17:
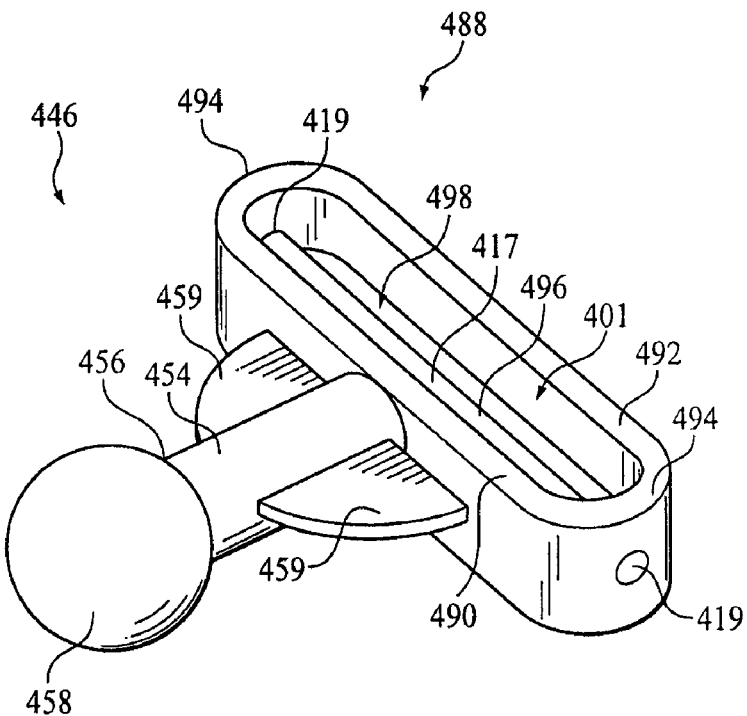
FIG. 17 is a perspective view of a second alternative strap connector in the patient interface assembly of FIG. 15 according to the principles of an exemplary embodiment of the present invention.

FIGS. 17-19B depict various alternative embodiments of the strap connector. FIG. 17 shows a second alternative strap connector 446 which includes a locking portion 488 having a first elongate member 490 and a second elongate member 492. The elongate members terminate at a pair of side members 494. The locking portion 488 also includes a divider 496 defining a first opening 498 and a second opening 401. As in the previous embodiment, strap connector 446 further includes a post portion 454 extending from the midpoint of the locking portion 488. The strap connector 446 includes web portions 459 to support post portion 454. At a distal end 456 of post portion 454 is a bulbous portion 458 of a diameter that is larger, e.g., twice the diameter, of post portion 454. It can be appreciated that shapes other than the sphere shown in the figures are contemplated for bulbous portion 458.

In contrast to the strap connector described in the previous embodiment, divider 496 is a separate pin member 417 inserted into holes 419 formed in locking portion 488 rather than being formed integrally with locking portion 488. The separate member may have a variety of cross-sectional geometries such as a cylindrical, rectangular, and the like. The divider may be secured in place by a friction fit, adhesive, or a variety of other attachment methods well-known in the art. The strap connector also includes a post portion 454 extending from the midpoint of the locking portion 488 and web portions 459 to support post portion 454. At a distal end 456 of post portion 454, is a bulbous portion 458.

Figure 18A:
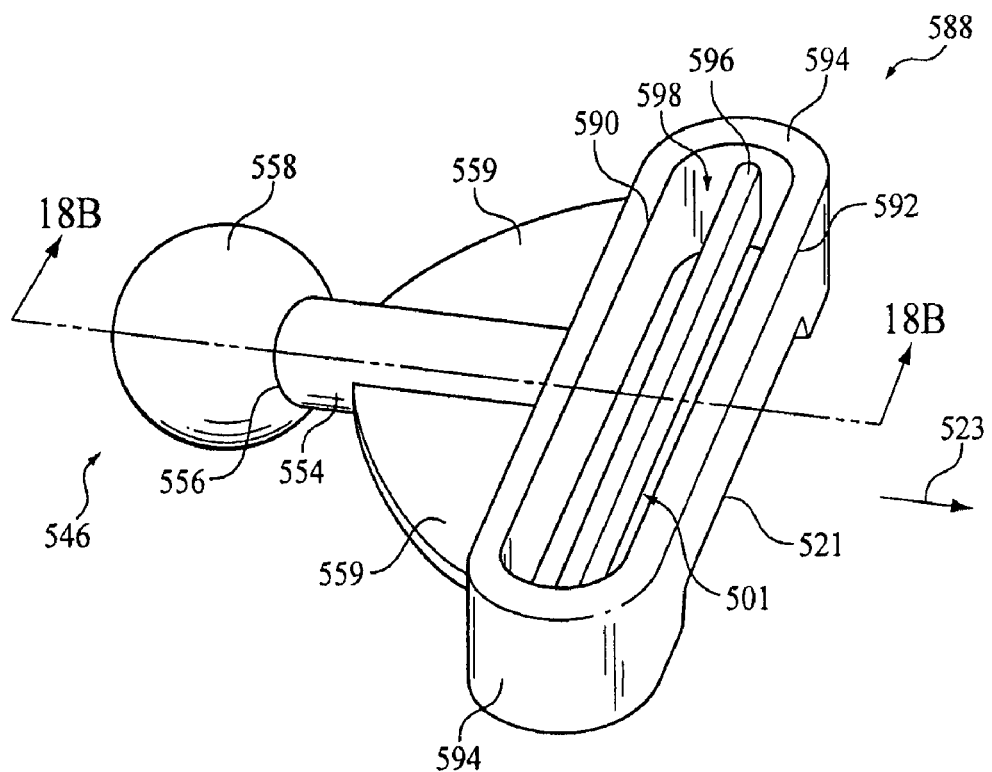
FIG. 18A is a perspective view of a third alternative strap connector in the patient interface assembly of FIG. 15 according to the principles of an exemplary embodiment of the present invention.
Figure 18B:
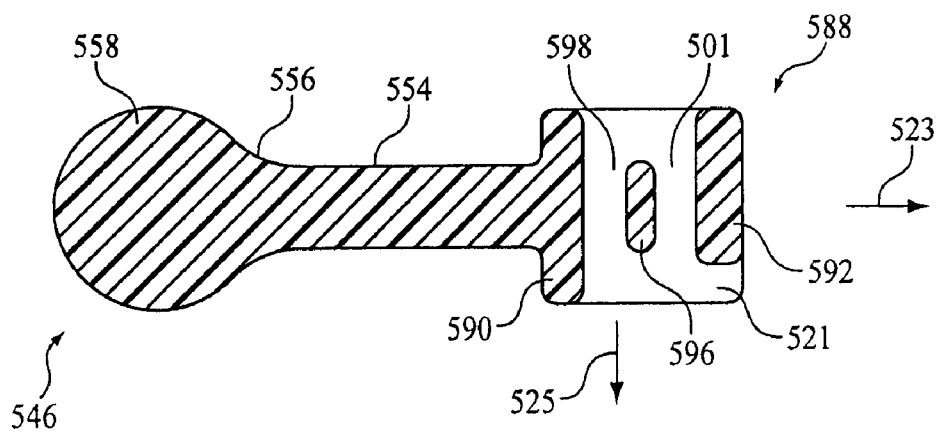

FIGS. 18A and 18B depict a third alternative embodiment of the strap connector. As in the previous embodiment, strap connector 546 includes a post portion 554 extending from the midpoint of the locking portion 588. The strap connector 546 includes web portions 559 to support post portion 554. At a distal end 556 of post portion 554 is a bulbous portion 558 of a diameter that is larger, e.g., twice the diameter, of post portion 554.

Locking portion 588 has a first elongate member 590 and a second elongate member 592. The elongate members terminate at a pair of side members 594. The locking portion 588 also includes a divider 596 defining a first opening 598 and a second opening 501. Unlike the divider disclosed in the previous embodiment, divider 596 has a rectangular cross-section with rounded corners. The divider of this embodiment has a height that is less than the height of the elongate members 590, 592. As a result, the strap will be nested within the locking portion. In addition, the second locking portion includes a groove 521. As a tensile force is applied in the direction of arrow 523, the strap will be locked in place. However, if the strap is turned 90 degrees and pulled in the direction of arrow 525 the strap can be slide through the locking portion.

Figure 19A:
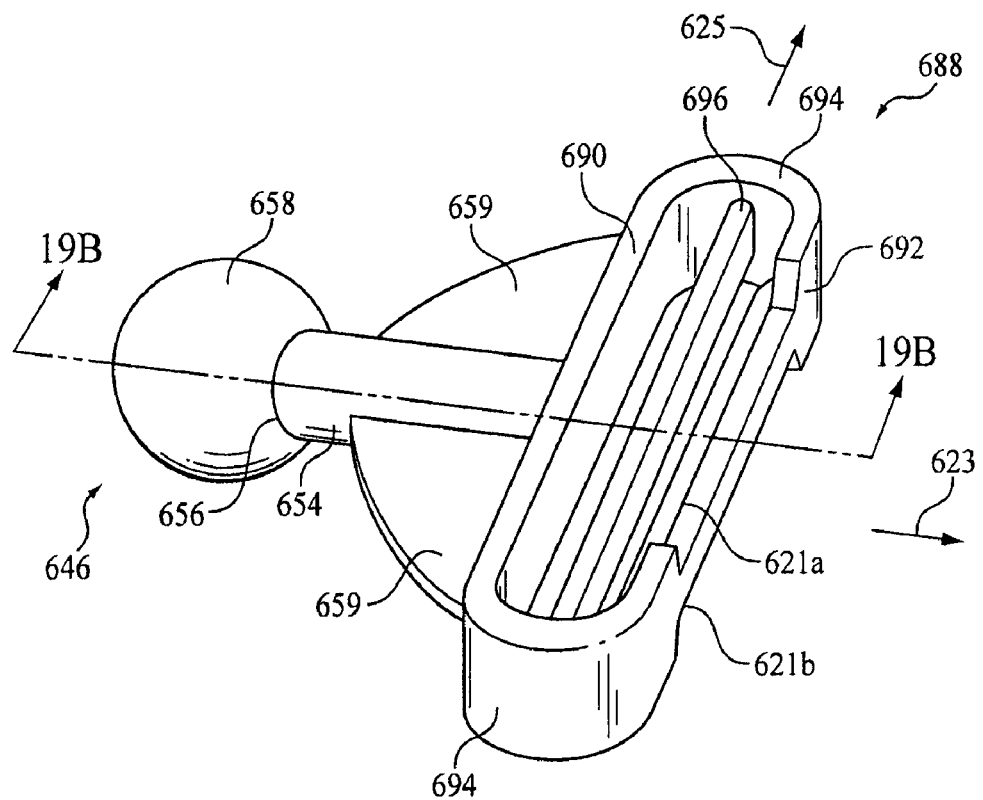
FIG. 19A is a perspective view of a fourth alternative strap connector in the patient interface assembly of FIG. 15 according to the principles of an exemplary embodiment of the present invention.
Figure 19B:
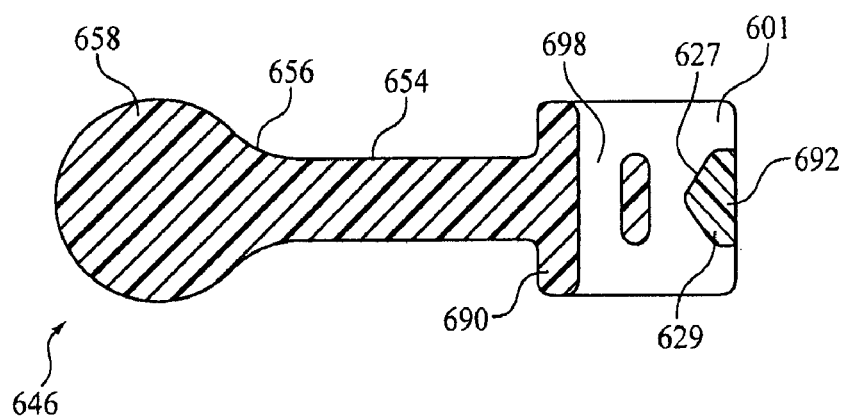
FIG. 19B is a cross-sectional view of the fourth alternative strap connector of FIG. 19A.

FIGS. 19A and 19B depict a fourth alternative embodiment of the strap connector. As in the previous embodiment, strap connector 646 includes a post portion 654 extending from the midpoint of the locking portion 688. The strap connector 646 includes web portions 659 to support post portion 654. At a distal end 656 of post portion 654 is a bulbous portion 658 of a diameter that is larger, e.g., twice the diameter, of post portion 654. It can be appreciated that shapes other than the sphere shown in the figures are contemplated for bulbous portion 658.

Locking portion 688 has a first elongate member 690 and a second elongate member 692. The elongate members terminate at a pair of side members 694. The locking portion 688 also includes a divider 696 defining a first opening 698 and a second opening 601. Divider 696 has a rectangular cross-section with rounded corners, and has a height that is less than the height of the elongate members 690, 692. As a result, the strap will be nested within the locking portion. In addition, the second locking portion includes a groove 621. As a tensile force is applied in the direction of arrow 623, the strap will be locked in place. However, if the strap is turned 90 degrees and pulled in the direction of arrow 625 the strap can be slide through the locking portion. Unlike the previous embodiment, the second elongate member 692 has a triangular cross-sectional shape having a first ramped portion 627 and a second ramped portion 629. This triangular shaped elongate member operates to engage the strap when pulled in the direction of arrow 623.

Figure 20A:
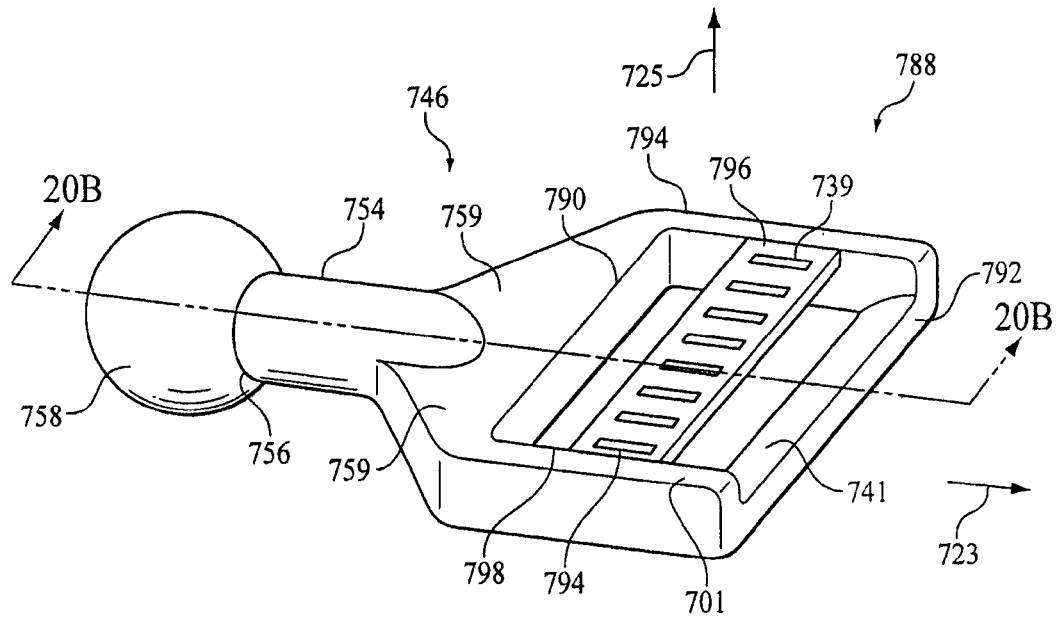
FIG. 20A is a perspective view of a fifth alternative strap connector in the patient interface assembly of FIG. 15 according to the principles of an exemplary embodiment of the present invention.
Figure 20B:
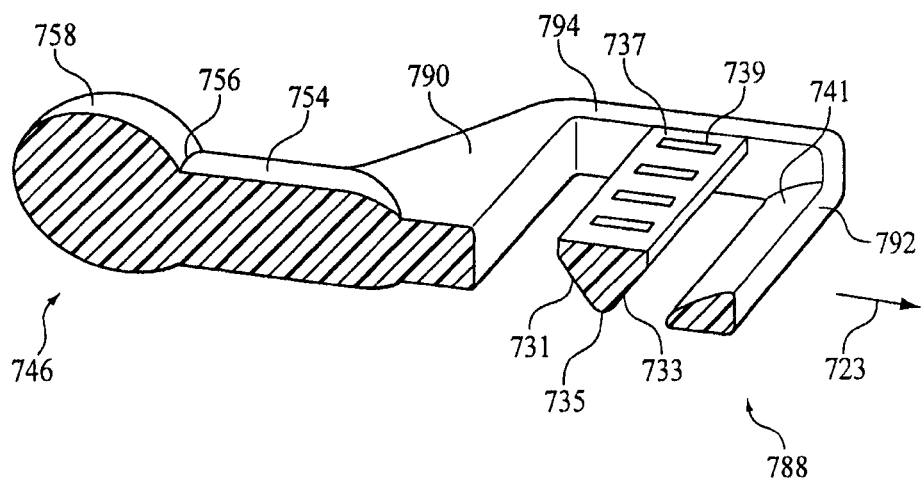
FIG. 20B is a cross-sectional view of the fifth alternative strap connector of FIG. 20A.

FIGS. 20A and 20B depict a fifth alternative embodiment of the strap connector. As in the previous embodiment, strap connector 746 further includes a post portion 754 extending from the midpoint of the locking portion 788. In a preferred embodiment, post portion 754 is substantially rigid. The strap connector 746 includes web portions 759 to support post portion 754. At a distal end 756 of post portion 754 is a bulbous portion 758 of a diameter that is larger, e.g., twice the diameter, of post portion 754. It can be appreciated that shapes other than the sphere shown in the figures are contemplated for bulbous portion 758.

The headgear straps are connected to the mask via locking portions 788. Locking portions include elongate members 790, 792 between a pair of side members 794. A divider 796 is located between the elongate members 790, 792 to define a pair of openings 798, 701. Divider 796 has a triangular cross-section defined by lower surface 731, 733 which terminate at an apex 735. The divider further includes a top surface 737 which includes nubs 739. Elongate member 792 includes a ramp portion 741. One of ordinary skill in the art can best appreciate that when the strap is pulled in the direction indicated by arrow 723 the strap will synch-in since it is forced to bend outward in one direction along angled surfaces 731, 733 and outward in the opposite direction due to the second elongate member 792. This effect is further achieved due to the additional friction resulting from nubs 739. However, if the strap is pulled in the direction of arrow 725, nubs 739 will release the strap. Moreover, the strap will also be able to easily slide over lower side 733 and ramp portion 741.

Figure 21A:
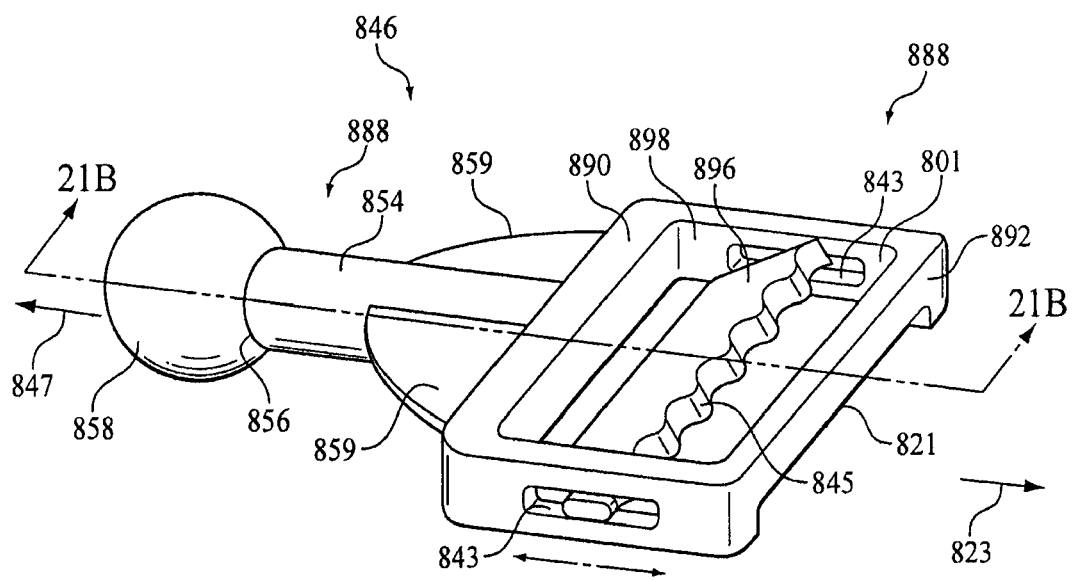
FIG. 21A is a perspective view of a sixth alternative strap connector in the patient interface assembly of FIG. 15 according to the principles of an exemplary embodiment of the present invention.
Figure 21B:
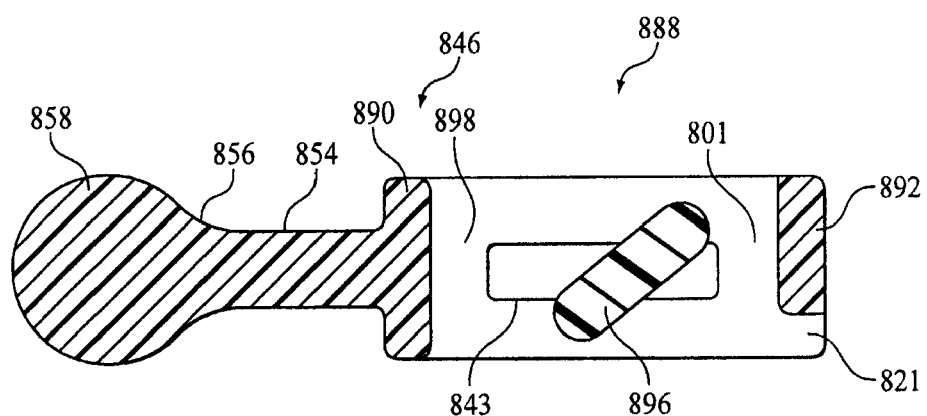
FIG. 21B is a cross-sectional view of the sixth alternative strap connector of FIG. 21A.

A sixth alternative embodiment is shown in FIGS. 21A and 21B. As in the previous embodiment, strap connector 846 further includes a post portion 854 extending from the midpoint of the locking portion 888. The strap connector 846 includes web portions 859 to support post portion 854. At a distal end 856 of post portion 854 is a bulbous portion 858 of a diameter that is larger, e.g., twice the diameter, of post portion 854. It can be appreciated that shapes other than the sphere shown in the figures are contemplated for bulbous portion 858.

In this embodiment, the locking portion 888 has a pair of openings 898, 801 defined by a first elongate member 890, a second elongate member 892, and a divider 896. Unlike the previous embodiment, divider 896 is captured in a pair of slots 843. In addition, divider 896 is angled upward and includes a plurality of serrations 845. The strap is weaved in under groove 821, through opening 898, over serrations 845, through opening 801, and then back through groove 821. As the strap is pulled in the direction of arrow 823, divider 896 slides along slots 843 to bend the strap and hold it between second elongate member 892 and divider 896. To release the strap from the strap connector, the tensile force in direction 823 is released. Next the user will slide divider 896 in the direction of arrow 847.

In the illustrated embodiments, the first connectors are shown located at the lower sides of the mask shell. However, the present invention contemplates providing these connecting elements at other locations on the mask and oriented in any desired direction. For example, the first connector can be provided on the forehead assembly. The present invention also contemplates that the male-female orientation of the first connectors and strap connectors can be reversed. In other words, the ball element, which is shown in FIG. 1 as being on the strap connector, can be provided on the mask, and the socket element, which is shown in FIG. 1 as being on the first connector, can provided on the strap connector.

Figure 22:
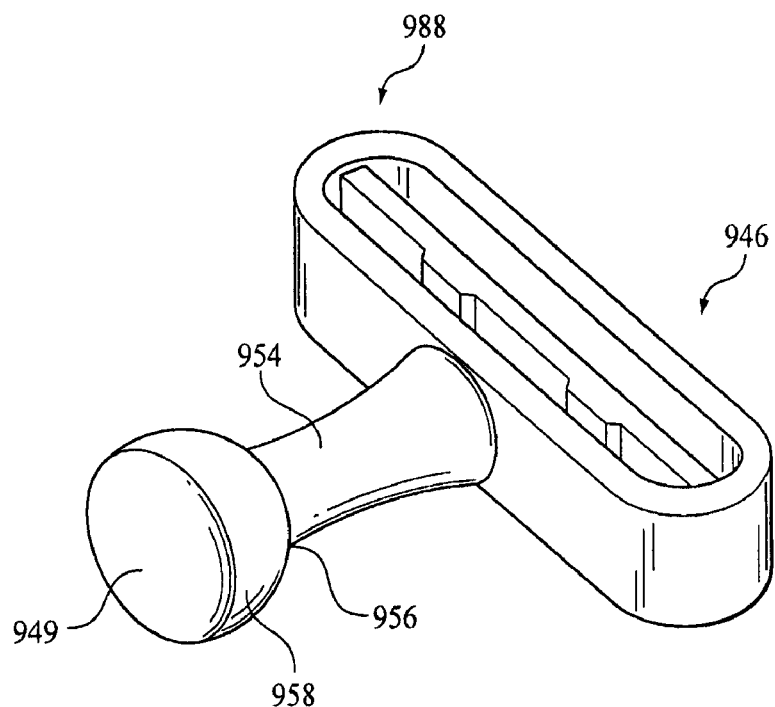
FIG. 22 is a perspective view of a fifth alternative strap connector.
Figure 23:
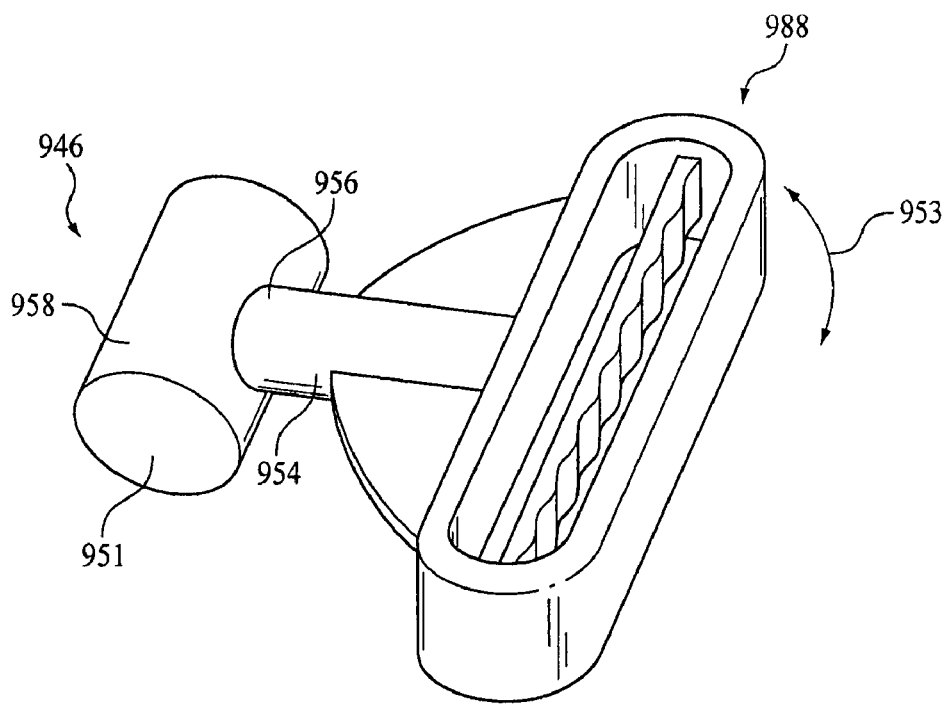
FIG. 23 is a perspective view of a sixth alternative strap connector.
Figure 24:
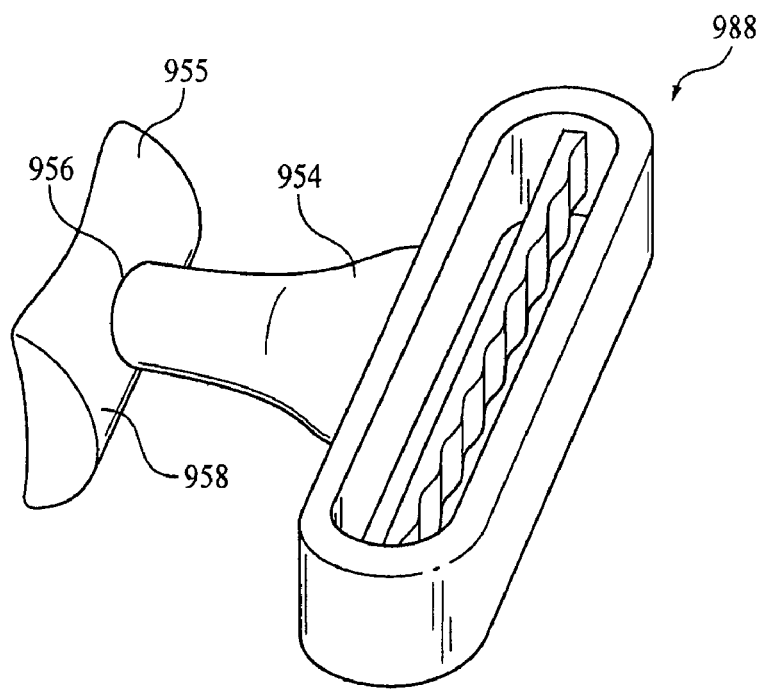
FIG. 24 is a perspective view of a seventh alternative strap connector.

In yet another alternative embodiment, the strap connector may have a variety of other configurations. As seen in FIGS. 22-24, strap connector 946 includes a locking portion 988. The locking portion is connected to a post portion 954 having a distal end 956. However, unlike the previous embodiments, the bulbous portion 958 has a variety of different configurations. For instance, as seen in FIG. 22, the bulbous portion may be hemispherical portion 949 or some other portion of a sphere. Alternatively, as seen in FIG. 23, the bulbous portion may be a cylindrical portion 951. This will permit the device to pivot in the direction of arrow 953 when connected to the first connector, thus restricting it from rotating from side-to-side or spinning about its axis as a hemispherical bulbous portion would permit. Alternatively, as seen in FIG. 24, the bulbous portion may be a partial cylindrical portion 955.

Figure 25:
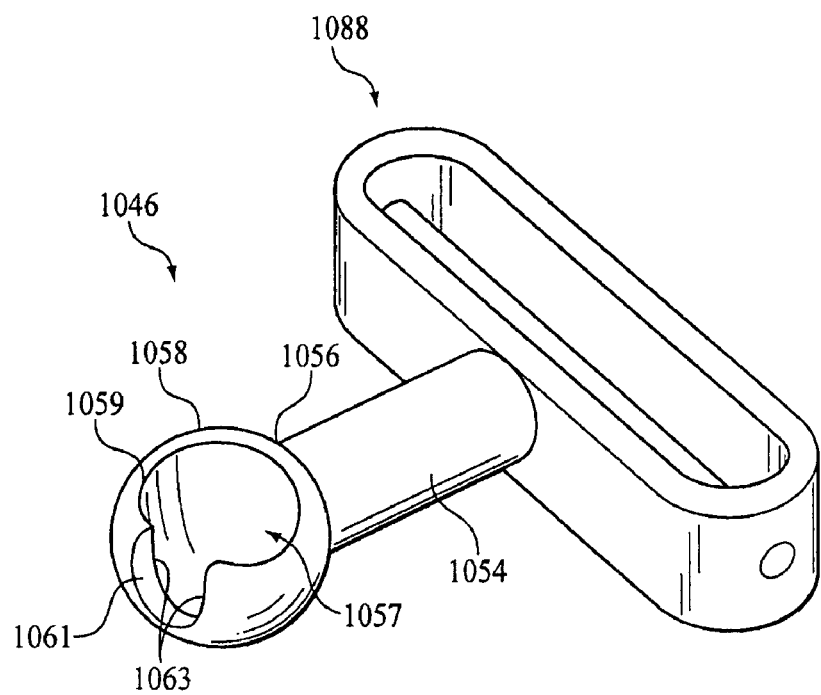
FIG. 25 is a perspective view of an eighth alternative strap connector.

In yet another alternative embodiment, as shown in FIG. 25 strap connector 1046 includes a locking portion 1088. The locking portion is connected to a post portion 1054 having a distal end 1056. Unlike the previous embodiments, the bulbous portion 1058 includes a socket 1057. Socket 1057 has a large opening 1059 and a smaller opening 1061 surrounded by a pair of shoulders 1063. This bulbous portion has a generally spherical shape. However, one of ordinary skill in the art can best appreciate that this shape of the bulbous portion may have a variety of other shapes. For instance, the bulbous portion may have any of the shapes depicted in FIGS. 22-24.

Figure 26:
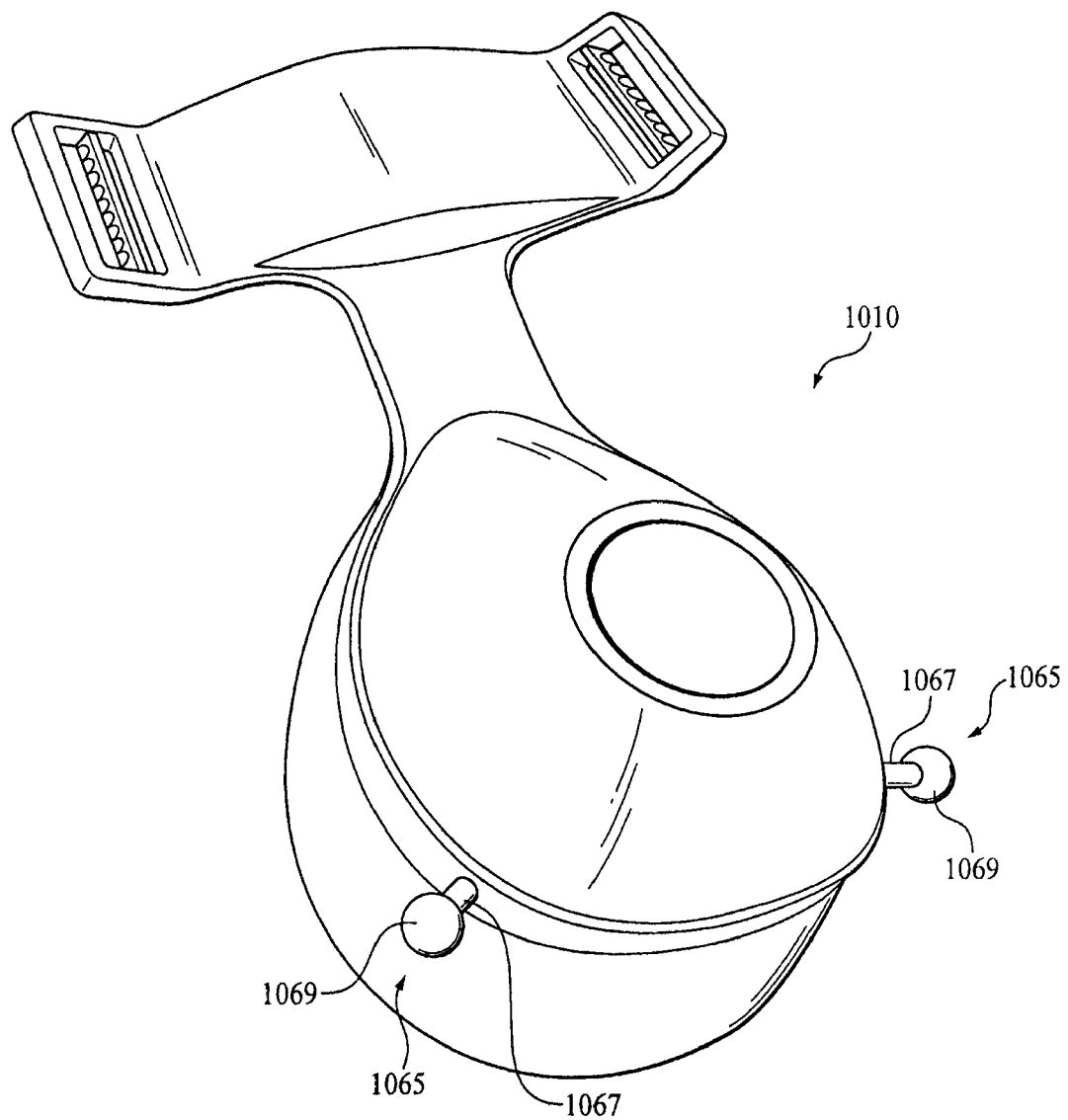
FIG. 26 is a perspective view of an alternative embodiment of the gas delivery mask.

The unique configuration of this strap connector permits it to be used with masks that have first connectors, as seen in FIG. 1. Alternatively, this strap connector may also be used with mask 1010 having a bulbous connector 1065 as seen in FIG. 26. The bulbous connector 1065 includes a post portion 1067 terminating at a bulbous portion 1069. Bulbous portion 1069 may be inserted into socket 1057 of bulbous portion 1058 and retained in place by shoulders 1063. As such, this strap connector may be used with masks having either socket-style connectors or bulbous-style connectors.

The inventors contemplate that the features of one embodiment of the present invention may be substituted or combined with the features of the other embodiments of the present invention. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A gas delivery mask comprising:
    a shell;
    a first connector associated with the shell;
    a second connector adapted to be connected to a headgear having at least one strap for securing the mask on a user, the second connector further includes a locking portion and a bulbous portion releasably and rotateably connecting the first connector and the second connector,
    wherein the locking portion comprises at least two openings, and at least one divider located between the two openings, wherein the second connector comprises a post portion that has an axis and connects the bulbous portion to the locking portion, and wherein the at least one divider has a direction of elongation that is coplanar with and perpendicular to the axis.

2. The gas delivery mask of claim 1, wherein the first connector comprises a pair of a parallel walls and a curved notched wall abutting the parallel walls and wherein the bulbous portion is adapted for insertion in the notched wall of the first connector so as to permit 360 degrees of rotation about the axis of the post portion.

3. The gas delivery mask of claim 1, wherein the locking portion is a locking clamp.

4. The gas delivery mask as recited in claim 1, wherein the at least two openings are shaped and positioned to facilitate threading of the at least one strap through the at least two openings in a manner that adjustably locks the at least one strap to the second connector.

5. The gas delivery mask as recited in claim 1, wherein the divider is movable relative to the at least two openings.

6. A gas delivery mask comprising:
    a shell;
    a first connector associated with the shell, wherein the first connector is a female connector;
    a second connector adapted to be connected to a headgear having at least one strap for securing the mask on a user, the second connector further includes a locking portion and a bulbous portion releasably and rotateably connecting the first connector and the second connector,
    wherein the first connector extends outwardly from the shell and comprises a first pair of a parallel walls and a curved notched wall abutting the first pair of parallel walls, the curved notched wall curving downwardly toward the shell and comprising a second pair of parallel walls defining a notch therebetween, wherein the notch extends throughout a length of the curved notched wall and has an area of reduced width near an upper, distal edge of the second pair of parallel walls.

7. The gas delivery mask of claim 6, wherein the first connector is integrally formed with the shell.

8. The gas delivery mask of claim 7, wherein the second connector is a corresponding male connector.

9. A gas delivery mask comprising:
a shell;
a forehead support extending from the shell;
a forehead member attached to the forehead support, the forehead member including a locking member that is shaped and adapted to adjustably lock a first headgear strap to the forehead member at any of a plurality of positions along the first headgear strap, wherein the locking member further comprises:
at least two openings, the at least two openings being shaped and positioned to facilitate threading of the first headgear strap through the at least two openings in a manner that adjustably locks the first headgear strap to the locking member; and
at least one divider located between the two openings.

10. The gas delivery mask of claim 9, wherein the locking member is a locking clamp.

11. The gas delivery mask of claim 9, further comprising:
a first connector associated with the shell; and
a second connector adapted to be connected to a second headgear strap for securing the mask on a user, the second connector further including a locking portion that is shaped and adapted to adjustably lock the second headgear strap to the second connector at any of a plurality of positions along the second headgear strap.

12. The gas delivery mask of claim 11, wherein the first connector is a female connector integrally formed with the shell.

13. The gas delivery mask of claim 12, wherein the first connector comprises a pair of a parallel walls and a curved notched wall abutting the parallel walls.

14. The gas delivery mask of claim 11, wherein the locking portion and locking member each comprise a locking clamp.

15. The gas delivery mask of claim 13, wherein the second connector further comprises:
an elongated portion;
a post portion having an axis and extending from the elongated portion; and a bulbous end portion associated with the distal end of the post portion, the bulbous end portion adapted for insertion in the notched wall of the first connector so as to permit 360 degrees of rotation about the axis of the post portion.

16. The gas delivery mask of claim 12, wherein the second connector is a corresponding male connector.

17. A gas delivery mask comprising:
a shell;
a first connector associated with the shell;
a second connector adapted to be connected to a headgear having at least one strap for securing the mask on a user, the second connector including a locking portion, a post portion connected to the locking portion and a bulbous portion attached to a distal end of the post portion, the bulbous portion releasably and rotateably connecting the first connector and the second connector, the bulbous portion having a socket provided therein.

18. The gas delivery mask as recited in claim 17, wherein the first connector is a bulbous connector.

19. The gas delivery mask as recited in claim 17, wherein the socket comprises a large opening and a small opening adjacent the large opening.

20. The gas delivery mask as recited in claim 17, wherein the socket is constructed and shaped to have a bulbous connector releasably secured therein.

21. A gas delivery mask comprising:
a shell;
a first connector associated with the shell; and
a second connector adapted to be connected to a headgear having at least one strap for securing the mask on a user,
wherein one of the first and second connectors comprises a first male connector while the other of the first and second connectors comprises a first female connector, the male and female connectors being releasably and rotatably connectable for securing the first and second connectors together, and
wherein the first male connector includes a post portion and a bulbous portion attached to a distal end of the post portion, the bulbous portion having a second female connector provided therein that is constructed and arranged to releasably and rotatably connect to a second male connector.

* * * * *